(12) United States Patent
Cao et al.

(10) Patent No.: US 8,475,839 B2
(45) Date of Patent: *Jul. 2, 2013

(54) SOLID DOSAGE FORMS OF VALSARTAN, AMLODIPINE AND HYDROCHLOROTHIAZIDE AND METHOD OF MAKING THE SAME

(75) Inventors: Yu Cao, Parsippany, NJ (US); Yatindra Joshi, Princeton, NJ (US); Ping Li, Basking Ridge, NJ (US); Madhusudhan Pudipeddi, Mumbai (IN); Alan E Royce, Saylorsburg, PA (US); Robert F Wagner, Hillsborough, NJ (US); Jiahao Zhu, Whippany, NJ (US)

(73) Assignee: Novartis AG, Basel (CH)

(*) Notice: Subject to any disclaimer, the term of this patent is extended or adjusted under 35 U.S.C. 154(b) by 0 days.

This patent is subject to a terminal disclaimer.

(21) Appl. No.: 13/342,533

(22) Filed: Jan. 3, 2012

(65) Prior Publication Data

US 2012/0164218 A1 Jun. 28, 2012

Related U.S. Application Data

(63) Continuation of application No. 11/915,096, filed as application No. PCT/US2007/072097 on Jun. 26, 2007, now abandoned.

(60) Provisional application No. 60/805,883, filed on Jun. 27, 2006.

(51) Int. Cl.

| A61K 31/549 | (2006.01) |
| A61K 9/28 | (2006.01) |
| A61P 9/12 | (2006.01) |
| A61P 9/04 | (2006.01) |
| A61P 9/10 | (2006.01) |
| A61P 9/00 | (2006.01) |

(52) U.S. Cl.
USPC .... 424/464; 427/2.14; 514/223.2; 514/223.5; 514/355; 514/381

(58) Field of Classification Search
None
See application file for complete search history.

(56) References Cited

U.S. PATENT DOCUMENTS

| 6,057,344 | A | 5/2000 | Young | 514/356 |
| 6,869,970 | B2 | 3/2005 | Marti | |
| 2003/0152622 | A1* | 8/2003 | Louie-Helm et al. | 424/468 |
| 2003/0216384 | A1* | 11/2003 | Stokes | 514/223.5 |
| 2004/0087484 | A1* | 5/2004 | Sahota | 514/2 |
| 2005/0018632 | A1 | 1/2005 | Lee et al. | |
| 2005/0222137 | A1 | 10/2005 | Shetty et al. | |

FOREIGN PATENT DOCUMENTS

| WO | WO02/43807 | 6/2002 |
| WO | 03/097045 | 11/2003 |
| WO | WO 03/097045 | 11/2003 |
| WO | WO2005/070462 | 8/2005 |
| WO | WO 2005/112870 A1 | 12/2005 |
| WO | WO 2005/112898 A1 | 12/2005 |

OTHER PUBLICATIONS

Wald, N. J. et al: "A strategy to reduce cardiovascular disease by more than 80%", Jun. 28, 2003; BMJ (Clinical Research Ed.); vol. 326, No. 7404, p. 1419.

Ansel (Pharmaceutical Dosage Forms and Drug Delivery Systems 1999, 7th Ed. pp. 198 and 201) 3 pages.

Gunsel WC, et al, [medical textbook since B.C.] "Compression-Coated & Layer Tablets", Pharmaceutical Dosage Forms: Tablets, $2^{nd}$ edition. vol. 1, chapter 5. pp. 247-284 (1989).

* cited by examiner

*Primary Examiner* — Ernst Arnold
(74) *Attorney, Agent, or Firm* — Daniel Woods

(57) ABSTRACT

Monolayer, bilayer and trilayer solid dosage forms of a combination of valsartan, amlodipine and hydrochlorothiazide are made.

7 Claims, No Drawings

SOLID DOSAGE FORMS OF VALSARTAN, AMLODIPINE AND HYDROCHLOROTHIAZIDE AND METHOD OF MAKING THE SAME

This application is a continuation U.S. patent application Ser. No. 11/915,096, filed Nov. 20, 2007, which is a National Phase application of PCT2007/072097, filed Jun. 26, 2007, which claims benefit of Provisional Application No. 60/805,883, filed Jun. 27, 2006.

BACKGROUND OF THE INVENTION

1. Field of the Invention

The present invention is directed to solid dosage formulations containing a combination of valsartan, amlodipine and a diuretic such as hydrochlorothiazide, as well as to methods of making such solid dosage forms and a method of treating a subject with such solid dosage forms.

2. Related Background Art

The development of fixed-combination solid dosage formulations of certain active ingredients is challenging. As used herein, "fixed-combination" refers to a combination of two or more drugs or active ingredients presented in a single dosage unit such as a tablet or a capsule; further as used herein, "free-combination" refers to a combination of two or more drugs or active ingredients dosed simultaneously but as two or more dosage units. When formulating fixed-combination solid dosage formulations, the objective is to provide a patient-convenient combination dosage form of active ingredients that is bioequivalent to the corresponding free-combination of the same active ingredients and/or delivers a superior pharmacodynakic effect than the individual components. Development of fixed-combination dosage formulations that are bioequivalent to the free-combination is challenging due to the multiplicity of challenges arising from pharmacokinetic and pharmaceutical properties of the drugs sought to be combined.

For example, valsartan has an absolute oral bioavailability of only about 25% with a wide range of 10-35%. Valsartan also has pH dependent solubility whereby it ranges from very slightly soluble in an acidic environment to soluble in a neutral environment of the gastrointestinal tract. Further, development of a patient-convenient oral dosage form of valsartan is challenging due to its low bulk density. Amlodipine besylate is slightly soluble in water and has an absolute bioavailability of 64-90%. Hydrochlorothiazide is slightly soluble in water and has an oral bioavailability 60-80%. As a result of these complex biopharmaceutical properties, development of a fixed-combination dosage form of valsartan, amlodipine and hydrochlorothiazide that is bioequivalent to a free-combination thereof is challenging.

Accordingly, a fixed-combination solid dosage formulation of valsartan, amlodipine and hydrochlorothiazide that is bioequivalent to the corresponding free-combination would be desirable.

SUMMARY OF THE INVENTION

In a first embodiment, the present invention is directed to a solid dosage form comprising a combination of valsartan, amlodipine and hydrochlorothiazide, and pharmaceutically acceptable additives suitable for the preparation of solid dosage forms. In preferred embodiments of this invention, amlodipine free base is provided in the form of amlodipine besylate, and the pharmaceutically acceptable additives are selected from diluents, disintegrants, glidants, lubricants, binders, colorants and combinations thereof.

In certain preferred embodiments of this invention, the solid dosage form is a monolayer tablet. In other preferred embodiments of this invention, the solid dosage form is a bilayer tablet, e.g., having the valsartan and the hydrochlorothiazide in one layer and the amlodipine in another layer or having the valsartan in one layer and the amlodipine and the hydrochlorothiazide in another layer or having the valsartan and the amlodipine in one layer and the hydrochlorothiazide in another layer. In other preferred embodiments of this invention, the solid dosage form is a trilayer tablet, e.g., having all three actives in separate layers. The amount of valsartan employed in such solid dosage forms, monolayer or bilayer, preferably ranges from about 40 mg to about 640 mg, preferably 80 mg to 640 mg, and more preferably is 160 mg or 320 mg. The amount of amlodipine employed in such solid dosage forms, monolayer or bilayer, preferably ranges from about 2.5 mg to about 20 mg, and more preferably is 5 mg or 10 mg. The amount of hydrochlorothiazide employed in such solid dosage forms, monolayer or bilayer, preferably ranges from about 6.25 mg to about 50 mg, and more preferably is 12.5 mg or 25 mg.

In a second embodiment, the present invention is directed to a method of making a solid dosage form of valsartan, amlodipine and HCTZ comprising the steps of (a) blending valsartan, amlodipine, hydrochlorothiazide and pharmaceutically acceptable additives to form a blended material; (b) sieving the blended material to form a sieved material; (c) blending the sieved material to form a blended/sieved material; (d) compacting the blended/sieved material to form a compacted material; (e) milling the compacted material to form a milled material; (f) blending the milled material to form blended/milled material; and (g) compressing the blended/milled Material to form a monolayer solid dosage form. A preferred embodiment of this invention also includes an optional step, step (h) film coating the monolayer solid dosage form.

In a third embodiment, this invention is directed to solid dosage forms of valsartan, amlodipine and HCTZ made according to the method of the second embodiment.

In a fourth embodiment, the present invention is directed to a method of making a solid dosage form of valsartan, amlodipine and HCTZ comprising the steps of a) blending valsartan and pharmaceutically acceptable additives to form a blended material; (b) sieving the blended material to form a sieved material; (c) blending the sieved material to form a blended/sieved material; (d) compacting the blended/sieved material to form a compacted material; (e) milling the compacted material to form a milled material; (f) blending the milled material with amlodipine and hydrochlorothiazide to form blended/milled material; and (g) compressing the blended/milled material to form a monolayer solid dosage form. A preferred embodiment of this invention also includes an optional step, step (h) film coating the monolayer solid dosage form.

In a fifth embodiment, this invention is directed to solid dosage forms of valsartan, amlodipine and HCTZ made according to the method of the fourth embodiment.

In a sixth embodiment, the present invention is directed to a method of making a solid dosage form of valsartan, amlodipine and HCTZ comprising the steps of a) blending valsartan, amlodipine, and pharmaceutically acceptable additives to form a blended material; (b) sieving the blended material to form a sieved material; (c) blending the sieved material to form a blended/sieved material; (d) compacting the blended/sieved material to form a compacted material; (e) milling the compacted material to form a milled material; (f) blending the milled material with hydrochlorothiazide to form blended/milled material; and (g) compressing the blended/milled material to form a monolayer solid dosage form. A preferred embodiment of this invention also includes an optional step, step (h) film coating the monolayer solid dosage form.

In a seventh embodiment, this invention is directed to solid dosage forms of valsartan, amlodipine and HCTZ made according to the method of the sixth embodiment.

In an eighth embodiment, the present invention is directed to a method of making a solid dosage form of valsartan, amlodipine and HCTZ comprising the steps of a) blending valsartan, hydrochlorothiazide, and pharmaceutically acceptable additives to form a blended material; (b) sieving the blended material to form a sieved material; (c) blending the sieved material to form a blended/sieved material; (d) compacting the blended/sieved material to form a compacted material; (e) milling the compacted material to form a milled material; (f) blending the milled material with amlodipine to form blended/milled material; and (g) compressing the blended/milled material to form a monolayer solid dosage form. A preferred embodiment of this invention also includes an optional step, step (h) film coating the monolayer solid dosage form.

In a ninth embodiment, this invention is directed to solid dosage forms of valsartan, amlodipine and HCTZ made according to the method of the eighth embodiment.

In a tenth embodiment, the present invention is directed to a method of making a solid dosage form of valsartan, amlodipine and HCTZ comprising the steps of (a) granulating valsartan, pharmaceutically acceptable additives and optionally hydrochlorothiazide to form a valsartan granulation; (b) granulating amlodipine, pharmaceutically acceptable additives and optionally hydrochlorothiazide to form an amlodipine granulation; and (c) compressing the valsartan granulation and the amlodipine granulation together to form a bilayer solid dosage form, wherein hydrochlorothiazide is present in the valsartan granulation and/or the amlodipine blend. In a preferred embodiment of the invention, step (a) comprises the steps of (a1) blending valsartan, pharmaceutically acceptable additives and optionally hydrochlorothiazide to form a blended material; (a2) sieving the blended material to form a sieved material; (a3) blending the sieved material to form a blended/sieved material; (a4) compacting the blended/sieved material to form a compacted material; (a5) milling the compacted material to form a milled material; and (a6) blending the milled material to form the valsartan granulation. In another preferred embodiment, step (b) comprises a granulation process with the steps of (b1) blending amlodipine, pharmaceutically acceptable additives and optionally hydrochlorothiazide to form a blended material; (b2) sieving the blended material to form a sieved material; (b3) blending the sieved material to form a blended/sieved material; (b4) compacting the blended/sieved material to form a compacted material; (b5) milling the compacted material to form a milled material; and (b6) blending the milled material to form an amlodipine granulation. Another preferred embodiment of this invention also includes an optional step, step (d) film coating the bilayer solid dosage form. Hydrochlorothiazide can be incorporated at step a1 and/or a6, and at step b1 and/or b6.

In a eleventh embodiment, this invention is directed to solid dosage forms of valsartan, amlodipine and HCTZ made according to the method of the tenth embodiment.

In another embodiment, this invention is directed to a method of making a solid dosage form of valsartan, amlodipine and HCTZ comprising the steps of (a) granulating valsartan, pharmaceutically acceptable additives and optionally amlodipine to form a valsartan granulation; (b) granulating hydrochlorothiazide, pharmaceutically acceptable additives and optionally amlodipine to form a hydrochlorothiazide granulation; and (c) compressing the valsartan granulation and the hydrochlorothiazide granulation together to form a bilayer solid dosage form, wherein amlodipine is present in the valsartan granulation and/or the hydrochlorothiazide blend. In a preferred embodiment of the invention, step (a) comprises the steps of (a1) blending valsartan, pharmaceutically acceptable additives and optionally amlodipine to form a blended material; (a2) sieving the blended material to form a sieved material; (a3) blending the sieved material to form a blended/sieved material; (a4) compacting the blended/sieved material to form a compacted material; (a5) milling the compacted material to form a milled material; and (a6) blending the milled material to form the valsartan granulation. In another preferred embodiment, step (b) comprises a granulation process with the steps of (b1) blending hydrochlorothiazide, pharmaceutically acceptable additives and optionally amlodipine to form a blended material; (b2) sieving the blended material to form a sieved material; (b3) blending the sieved material to form a blended/sieved material; (b4) compacting the blended/sieved material to form a compacted material; (b5) milling the compacted material to form a milled material; and (b6) blending the milled material to form a hydrochlorothiazide granulation. Another preferred embodiment of this invention also includes an optional step, step (d) film coating the bilayer solid dosage form. Amlodipine can be incorporated at step a1 and/or a6, and at step b1 and/or b6.

Yet another embodiment of the invention is directed to a method of treating hypertension, congestive heart failure, angina, myocardial infarction, arteriosclerosis, diabetic nephropathy, diabetic cardiac myopathy, renal insufficiency, peripheral vascular disease, stroke, left ventricular hypertrophy, cognitive dysfunction, headache, or chronic heart failure comprising administering a solid dosage form of valsartan, amlodipine and hydrochlorothiazide to a subject in need of such treatment. In a preferred embodiment, the solid dosage form is orally administered to the subject.

DETAILED DESCRIPTION

The present invention relates to solid dosage forms which contain a combination of valsartan, amlodipine and hydrochlorothiazide.

The first embodiment of the invention is directed to a solid dosage form comprising a combination of valsartan, amlodipine and hydrochlorothiazide, and pharmaceutically acceptable additives suitable for the preparation of solid dosage forms. The solid dosage forms of the present invention can take the form of monolayer tablets (having the valsartan, the amlodipine and the hydrochlorothiazide in one layer) or bilayer tablets (e.g., having the valsartan in one layer and the amlodipine and the hydrochlorothiazide in another layer or having the valsartan and the hydrochlorothiazide in one layer and the amlodipine in another layer or having the valsartan and the amlodipine in one layer and the hydrochlorothiazide in another layer) or trilayer tablets (e.g., having the valsartan, amlodipine and hydrochlorothiazide all in separate layers.) or a trilayer tablet of two active layers (amlodipine+HCTZ, amlodipine+valsartan) separated by a non-active layer and a third layer of valsartan or HCTZ or amlodipine.

Valsartan ((S)-N-valeryl-N-{[2'-(1H-tetrazole-5-yl)-biphenyl-4-yl]-methyl}-valine) suitable for use in the present invention can be purchased from commercial sources or can be prepared according to known methods. For example, the preparation of valsartan is described in U.S. Pat. No. 5,399,578, the entire disclosure of which is incorporated by reference herein. Valsartan may be used for purposes of this invention in its free form as well as in any suitable salt form.

Valsartan is employed in an amount typically ranging from about 40 mg to about 640 mg, preferably from about 80 mg to about 320 mg, and more preferably is about 160 mg or about 320 mg in a monolayer tablet or a bilayer tablet or a trilayer tablet. The amount of valsartan noted above refers to the amount of free valsartan or salt thereof present in a given solid dosage form.

Amlodipine (3-ethyl-5-methyl-2(2-aminoethoxymethyl)-4-(2-chlorophenyl)-1,4-dihydro-6-methyl-3,5-pyridinedicarboxylate benzenesulphonate) suitable for use in the present invention can be purchased from commercial sources or can be prepared according to known methods. Amlodipine may be used for purposes of this invention in its free form as well as in any suitable salt form; in a preferred embodiment of this invention, amlodipine free base is supplied to the solid dosage forms through the use of amlodipine besylate.

Amlodipine is employed in an amount ranging from 2.5 mg to about 20 mg, preferably from about 5 mg to about 10 mg, and more preferably is about 5 mg or about 10 mg in a monolayer tablet or a bilayer tablet or a trilayer tablet. The amount of amlodipine noted above refers to the amount of free amlodipine present in a given solid dosage form.

Hydrochlorothiazide suitable for use in the present invention can be purchased from commercial sources or can be prepared according to known methods. Hydrochlorothiazide may be used for purposes of this invention in its free form as well as in any suitable salt form.

Hydrochlorothiazide is employed in an amount ranging from 6.25 mg to about 50 mg, preferably from about 12.5 mg to about 25 mg, and more preferably is about 12.5 mg or about 25 mg in a monolayer tablet or a bilayer tablet or a trilayer tablet. The amount of hydrochlorothiazide noted above refers to the amount of free hydrochlorothiazide present in a given solid dosage form.

Pharmaceutically acceptable additives suitable for use in the present invention include, without limitation, diluents or fillers, disintegrants, glidants, lubricants, binders, colorants and combinations thereof. The amount of each additive in a solid dosage formulation may vary within ranges conventional in the art.

Suitable diluents include, without limitation, microcrystalline cellulose (e.g., cellulose MK GR), mannitol, sucrose or other sugars or sugar derivatives, low-substituted hydroxypropyl cellulose, di-calcium phosphate, lactose, and combinations thereof. When present, a diluent may be employed in an amount ranging from about 10% to about 80%, preferably from about 32% to about 51% by weight of the solid dosage form (prior to any optional film coating). For monolayer tablets, a diluent is preferably employed in an amount ranging from about 10% to about 80%, more preferably in an amount ranging from about 32% to about 39% by weight of the solid dosage form. For bilayer tablets, a diluent is preferably employed in an amount ranging from about 10% to about 80%, more preferably in an amount ranging from about 47% to about 51% by weight of the solid dosage form.

Suitable disintegrants include, without limitation, crospovidone, sodium starch glycolate, L-hydroxy propyl cellulose, croscarmellose sodium, and combinations thereof. When present, a disintegrant may be employed in an amount ranging from about 0.5% to about 50%, preferably from about 5% to about 14% by weight of the solid dosage form (prior to any optional film coating). For monolayer tablets, a disintegrant is preferably employed in an amount ranging from about 0.5% to about 50%, more preferably in an amount ranging from about 5% to about 14% by weight of the solid dosage form. For bilayer tablets, a disintegrant is preferably employed in an amount ranging from about 0.5% to about 50%, more preferably in an amount ranging from about 7% to about 10% by weight of the solid dosage form.

Suitable glidants include, without limitation, colloidal silicon dioxide (e.g., Aerosil 200), magnesium trisilicate, powdered cellulose, starch, talc and combinations thereof. When present, a glidant may be employed in an amount ranging from about 0.1% to about 10%, preferably from about 0.6% to about 0.8% by weight of the solid dosage form (prior to any optional film coating). For monolayer tablets, a glidant is preferably employed in an amount ranging from about 0.1% to about 10%, more preferably in an amount of about 0.75% by weight of the solid dosage form. For bilayer tablets, a glidant is employed in an amount ranging from about 0.1% to about 10%, more preferably in an amount of about 0.65% by weight of the solid dosage form.

Suitable lubricants include, without limitation, magnesium stearate, calcium stearate, aluminum or calcium silicate, stearic acid, cutina, PEG 4000-8000, talc and combinations thereof. When present, a lubricant may be employed in an amount ranging from about 0.1% to about 10%, preferably from about 2% to about 3% by weight of the solid dosage form (prior to any optional film coating). For monolayer tablets, a lubricant is preferably employed in an amount ranging from about 0.1% to about 10%, more preferably in an amount of about 2% by weight of the solid dosage form. For bilayer tablets, a lubricant is preferably employed in an amount ranging from about 0.1% to about 10%, more preferably in an amount of about 2% by weight of the solid dosage form.

Suitable binders include, without limitation, polyvinylpyrrolidone, hydroxypropylmethyl cellulose, hydroxypropyl cellulose, pregelatinized starch, microcrystalline cellulose (e.g., cellulose MK GR), and combinations thereof. When present, a binder may be employed in an amount ranging from about 0.5% to about 40%, preferably in an amount of about 10% by weight of the solid dosage form (prior to any optional film coating). For monolayer tablets, a binder is preferably employed in an amount ranging from about 0.5% to about 40%, more preferably in an amount of about 10% by weight of the solid dosage form. For bilayer tablets, a binder is preferably employed in an amount ranging from about 0.5% to about 40%, more preferably in an amount of about 10% by weight of the solid dosage form.

Suitable colorants include, without limitation, iron oxides such as yellow, red, and black iron oxide, and titanium dioxide and combinations thereof. When present, a colorant may be employed in an amount ranging from about 0.01% to about 0.1% by weight of the solid dosage form (prior to any optional film coating). In a preferred embodiment, monolayer tablets contain no colorant. Film coating for monolayer tablets are given in the example Tables The solid dosage forms of the first embodiment of the invention are monolayer or bilayer tablet dosage forms of suitable hardness, e.g., an average hardness ranging from about 60 N to about 350 N for monolayer forms and an average hardness ranging from about 100 N to about 350 N for bilayer forms. Such an average hardness is determined prior to the application of any film coating on the solid dosage forms. In that regard, a preferred embodiment of this invention is directed to solid dosage forms which are film-coated. Suitable film coatings are known and commercially available or can be made according to known methods. Typically the film coating material is a polymeric film coating material comprising materials such as hydroxypropylmethyl cellulose, polyethylene glycol, talc and colorant. Generally, a film coating material is applied in such an amount as to provide a film coating that ranges from about 1% to about 7% by weight of the film-coated tablet.

The second embodiment of the present invention is directed to a method of making a solid dosage form of valsartan, amlodipine and HCTZ comprising the steps of (a) blending valsartan, amlodipine, hydrochlorothiazide and pharmaceutically acceptable additives to form a blended material; (b) sieving the blended material to form a sieved material; (c) blending the sieved material to form a blended/sieved material; (d) compacting the blended/sieved material to form a compacted material; (e) milling the compacted material to form a milled material; (f) blending the milled material to form blended/milled material; and (g) compressing the blended/milled material to form a monolayer solid dosage form. The details regarding the valsartan, amlodipine, hydrochlorothiazide and pharmaceutically acceptable additives, i.e., source, amount, etc., are as set forth above with regard to the first embodiment of the invention. This embodiment can be in the form of all possible permutations, e.g., valsartan may be blended alone and amlodipine and hydrochlorothiazide may be added in the final blending step.

In the first step of the method of the second embodiment, valsartan, amlodipine, hydrochlorothiazide and pharmaceutically acceptable additives are blended to form a blended material. Blending can be accomplished using any suitable means such as a diffusion blender or diffusion mixer. In the second step, the blended material is sieved to form a sieved material. Sieving can be accomplished using any suitable means. In the third step of the method of the second embodiment, the sieved material is blended to form a blended/sieved material. Again blending can be accomplished using any suitable means.

In the fourth step, the blended/sieved material is compacted to form a compacted material. Compacting can be accomplished using any suitable means. Typically compacting is accomplished using a roller compactor with a compaction force ranging from about 0.5 kN to about 90 kN, preferably about 20 kN to about 60 kN. Compaction may also be carried out by slugging the blended powders into large tablets that are then size-reduced.

In the fifth step of the method of the second embodiment, the compacted material is milled to form a milled material. Milling can be accomplished using any suitable means. In the sixth step, the milled material is blended to form blended/milled material. Here again blending can be accomplished using any suitable means. In the final step of the method of the second embodiment, the blended/milled material is compressed to form a monolayer solid dosage form. Compression can be accomplished using any suitable means. Typically compression is accomplished using a rotary tablet press. Compression force for such a rotary tablet press typically ranges from about 5 kN to about 40 kN.

Optionally, the method of the second embodiment comprises the step of (h) film coating the monolayer solid dosage form. The details regarding the film coating material, i.e., components, amounts, etc., are as described above with regard to the first embodiment of the invention. Film coating can be accomplished using any suitable means.

In a third embodiment, this invention is directed to solid dosage forms of valsartan made according to the method of the second embodiment.

In a fourth embodiment, the present invention is directed to a method of making a solid dosage form of valsartan amlodipine and HCTZ comprising the steps of a) blending valsartan and pharmaceutically acceptable additives to form a blended material; (b) sieving the blended material to form a sieved material; (c) blending the sieved material to form a blended/sieved material; (d) compacting the blended/sieved material to form a compacted material; (e) milling the compacted material to form a milled material; (f) blending the milled material with amlodipine and hydrochlorothiazide to form blended/milled material; and (g) compressing the blended/milled material to form a monolayer solid dosage form. A preferred embodiment of this invention also includes an optional step, step (h) film coating the monolayer solid dosage form.

In a fifth embodiment, this invention is directed to solid dosage forms of valsartan, amlodipine and HCTZ made according to the method of the fourth embodiment.

In a sixth embodiment, the present invention is directed to a method of making a solid dosage form of valsartan, amlodipine and HCTZ comprising the steps of a) blending valsartan, amlodipine, and pharmaceutically acceptable additives to form a blended material; (b) sieving the blended material to form a sieved material; (c) blending the sieved material to form a blended/sieved material; (d) compacting the blended/sieved material to form a compacted material; (e) milling the compacted material to form a milled material; (f) blending the milled material with hydrochlorothiazide to form blended/milled material; and (g) compressing the blended/milled material to form a monolayer solid dosage form. A preferred embodiment of this invention also includes an optional step, step (h) film coating the monolayer solid dosage form.

In a seventh embodiment, this invention is directed to solid dosage forms of valsartan, amlodipine and HCTZ made according to the method of the sixth embodiment.

In an eighth embodiment, the present invention is directed to a method of making a solid dosage form of valsartan, amlodipine and HCTZ comprising the steps of a) blending valsartan, hydrochlorothiazide, and pharmaceutically acceptable additives to form a blended material; (b) sieving the blended material to form a sieved material; (c) blending the sieved material to form a blended/sieved material; (d) compacting the blended/sieved material to form a compacted material; (e) milling the compacted material to form a milled material; (f) blending the milled material with amlodipine to form blended/milled material; and (g) compressing the blended/milled material to form a monolayer solid dosage form. A preferred embodiment of this invention also includes an optional step, step (h) film coating the monolayer solid dosage form.

In a ninth embodiment, this invention is directed to solid dosage forms of valsartan, amlodipine and HCTZ made according to the method of the eighth embodiment.

The tenth embodiment of the present invention is directed to a method of making a solid dosage form of valsartan, amlodipine and HCTZ comprising the steps of (a) granulating valsartan, pharmaceutically acceptable additives and optionally hydrochlorothiazide to form a valsartan granulation; (b) blending amlodipine, pharmaceutically acceptable additives and optionally hydrochlorothiazide to form an amlodipine blend; and (c) compressing the valsartan granulation and the amlodipine blend together to form a bilayer solid dosage form, wherein hydrochlorothiazide is present in the valsartan granulation and/or the amlodipine blend. The details regarding the valsartan, amlodipine, hydrochlorothiazide and pharmaceutically acceptable additives, i.e., source, amount, etc., are as set forth above with regard to the first embodiment of the invention.

In the first step of the method of the tenth embodiment, valsartan is granulated with pharmaceutically acceptable additives and optionally hydrochlorothiazide to form a valsartan granulation. Valsartan granulation can be accomplished by any suitable means. In a preferred embodiment of this invention, valsartan granulation is accomplished by (a1) blending valsartan, pharmaceutically acceptable additives and optionally hydrochlorothiazide to form a blended material; (a2) sieving the blended material to form a sieved material; (a3) blending the sieved material to form a blended/sieved material; (a4) compacting the blended/sieved material to form a compacted material; (a5) milling the compacted material to form a milled material; and (a6) blending the milled material to form the valsartan granulation. Hydrochlorothiazide can be incorporated at step a1 and/or a6.

The blending of step (a1) can be accomplished using any suitable means. Typically the valsartan, pharmaceutically acceptable additives and optionally the hydrochlorothiazide are dispatched to a suitable vessel such as a diffusion blender or diffusion mixer. The sieving of step (a2) can be accomplished using any suitable means. The blending of step (a3) can be accomplished using any suitable means. The compacting of step (a4) can be accomplished using any suitable means. Typically compacting is accomplished using a roller compactor with a compaction force ranging from about 0.5 kN to about 90 kN, preferably about 20-60 kN. Compaction may also be carried out by slugging the blended powders into large tablets that are then size-reduced. The milling of step (a5) can be accomplished using any suitable means. Typically the compacted material is milled through a screening mill. The blending of step (a6) can be accomplished using any suitable means. Preferably the milled material is blended, often with a pharmaceutically acceptable additive such as a lubricant, in a diffusion blender.

In the second step of the method of the tenth embodiment, amlodipine is blended with pharmaceutically acceptable additives and optionally hydrochlorothiazide to form an amlodipine blend. Amlodipine granulation can be accomplished by any suitable means. In a preferred embodiment, blending step (b) comprises the process of granulating amlodipine. Amlodipine granulation can be accomplished by any suitable means including but not limited wet granulation, dry granulation, melt granulation or dry blend. In a more preferred embodiment of this invention, amlodipine granulation is accomplished by (b1) blending amlodipine, pharmaceutically acceptable additives and optionally hydrochlorothiazide to form a blended material; (b2) sieving the blended material to form a sieved material; (b3) blending the sieved material to form a blended/sieved material; (b4) compacting the blended/sieved material to form a compacted material; (b5) milling the compacted material to form a milled material; and (b6) blending the milled material to form an amlodipine granulation. Hydrochlorothiazide can be incorporated at step b1 and/or b6. Hydrochlorothiazide can be incorporated by any suitable means including but not limited wet granulation, dry granulation, melt granulation or dry blend.

The blending of step (b1) can be accomplished using any suitable means. The sieving of step (b2) can be accomplished using any suitable means. The blending of step (b3) can be accomplished using any suitable means. The compacting of step (b4) can be accomplished using any suitable means. Typically compacting is accomplished using a roller compactor with a compaction force ranging from about 0.5 kN to about 90 kN, preferably about 20 kN to about 60 kN. The milling of step (b5) can be accomplished using any suitable means. Typically the compacted material is milled through a screening mill. The blending of step (b6) can be accomplished using any suitable means.

In the final step of the method of the tenth embodiment, the valsartan granulation and the amlodipine blend are compressed together to form a bilayer solid dosage form. Compression can be accomplished using any suitable means. Typically compression is accomplished using a bilayer rotary tablet press. Typical compression force ranges from about 5 kN to about 40 kN.

In this embodiment, hydrochlorothiazide is present in one of the valsartan granulation and the amlodipine blend. In other words, the inclusion of hydrochlorothiazide in the bilayer solid dosage form is not optional; only its placement in the same, i.e., in the valsartan layer or in the amlodipine layer, is variable. However, in other embodiments hydrochlorothiazide may be present alone in a separate layer.

Optionally, the method of the tenth embodiment comprises the step of (d) film coating the bilayer solid dosage form. The details regarding the film coating material, i.e., components, amounts, etc., are as described above with regard to the first embodiment of the invention. Film coating can be accomplished using any suitable means.

An eleventh embodiment of the present invention is directed to a bilayer solid dosage form of valsartan, amlodipine and HCTZ made according to the method of the tenth embodiment.

In another embodiment, this invention is directed to a method of making a solid dosage form of valsartan, amlodipine and HCTZ comprising the steps of (a) granulating valsartan, pharmaceutically acceptable additives and optionally amlodipine to form a valsartan granulation; (b) granulating hydrochlorothiazide, pharmaceutically acceptable additives and optionally amlodipine to form a hydrochlorothiazide granulation; and (c) compressing the valsartan granulation and the hydrochlorothiazide granulation together to form a bilayer solid dosage form, wherein amlodipine is present in the valsartan granulation and/or the hydrochlorothiazide blend. In a preferred embodiment of the invention, step (a) comprises the steps of (a1) blending valsartan, pharmaceutically acceptable additives and optionally amlodipine to form a blended material; (a2) sieving the blended material to form a sieved material; (a3) blending the sieved material to form a blended/sieved material; (a4) compacting the blended/sieved material to form a compacted material; (a5) milling the compacted material to form a milled material; and (a6) blending the milled material to form the valsartan granulation. In another preferred embodiment, step (b) comprises a granulation process with the steps of (b1) blending hydrochlorothiazide, pharmaceutically acceptable additives and optionally amlodipine to form a blended material; (b2) sieving the blended material to form a sieved material; (b3) blending the sieved material to form a blended/sieved material; (b4) compacting the blended/sieved material to form a compacted material; (b5) milling the compacted material to form a milled material; and (b6) blending the milled material to form a hydrochlorothiazide granulation. Another preferred embodiment of this invention also includes an optional step, step (d) film coating the bilayer solid dosage form. Amlodipine can be incorporated at step a1 and/or a6, and at step b1 and/or b6.

Yet another embodiment of the invention is directed to a method of treating hypertension, congestive heart failure, angina, myocardial infarction, arteriosclerosis, diabetic nephropathy, diabetic cardiac myopathy, renal insufficiency, peripheral vascular disease, stroke, left ventricular hypertrophy, cognitive dysfunction, headache, or chronic heart failure. The method comprises administering a solid dosage form of valsartan, amlodipine and hydrochlorothiazide to a subject in need of such treatment. In a preferred embodiment, the solid dosage form is orally administered to the subject.

Specific embodiments of the invention will now be demonstrated by reference to the following examples. It should be understood that these examples are disclosed solely by way of illustrating the invention and should not be taken in any way to limit the scope of the present invention.

Example 1

160/12.5/5 MG Tablet

A monolayer solid dosage form of valsartan, amlodipine and HCTZ was made using the ingredients set forth in Table 1 below.

TABLE 1

|   | Ingredient | (mg) | % |
|---|---|---|---|
| A | valsartan | 160.00 | 40.00 |
| B | hydrochlorothiazide | 12.50 | 3.13 |
| C | amlodipine besylate | 6.94* | 1.74 |
| D | microcrystalline cellulose | 154.56 | 38.64 |
| E | crospovidone | 54.00 | 13.50 |
| F | colloidal silicon dioxide | 3.00 | 0.75 |
| G | magnesium stearate (I) | 6.00 | 1.50 |
| H | magnesium stearate (II) | 3.00 | 0.75 |
|   | total | 400.00 |   |

*corresponds to 5 mg amlodipine free base

Ingredients A-G are placed into a diffusion blender and blended. Then, the blended material is sieved. Next, the sieved material is blended again in a diffusion blender. The blended/sieved material is then compacted using a roller compactor. The compacted material is milled through a screen and then blended with ingredient H in a diffusion blender. (This second blending step achieves the desired level of lubricant for the granulation and, in certain cases, combines sub-divided batches of ingredients A-G.) Next, the blended/milled material is compressed into monolayer solid dosage forms using a rotary tablet press, and the monolayer solid dosage forms are optionally film coated.

Ingredients A, C, D, E, F, and G are placed into a diffusion blender and blended. Then, the blended material is sieved. Next, the sieved material is blended again in a diffusion blender. The blended/sieved material is then compacted using a roller compactor. The compacted material is milled through a screen and then blended with ingredient B and H in a diffusion blender. (This second blending step achieves the desired level of B and H for the granulation and, in certain cases, combines sub-divided batches of ingredients A, C, D, E, F, and G.) Next, the blended/milled material is compressed into monolayer solid dosage forms using a rotary tablet press, and the monolayer solid dosage forms are optionally film coated.

Ingredients A, B, D, E, F, and G are placed into a diffusion blender and blended. Then, the blended material is sieved. Next, the sieved material is blended again in a diffusion blender. The blended/sieved material is then compacted using a roller compactor. The compacted material is milled through a screen and then blended with ingredient C and H in a diffusion blender. (This second blending step achieves the desired level of B and H for the granulation and, in certain cases, combines sub-divided batches of ingredients A, B, D, E, F, and G.) Next, the blended/milled material is compressed into monolayer solid dosage forms using a rotary tablet press, and the monolayer solid dosage forms are optionally film coated.

Ingredients A, D, E, F, and G are placed into a diffusion blender and blended. Then, the blended material is sieved. Next, the sieved material is blended again in a diffusion blender. The blended/sieved material is then compacted using a roller compactor. The compacted material is milled through a screen and then blended with ingredient B, C and H in a diffusion blender. (This second blending step achieves the desired level of B, C, and H for the granulation and, in certain cases, combines sub-divided batches of ingredients A, D, E, F, and G.) Next, the blended/milled material is compressed into monolayer solid dosage forms using a rotary tablet press, and the monolayer solid dosage forms are optionally film coated.

Example 2

160/12.5/10 Mg Tablet

A monolayer solid dosage form of valsartan, amlodipine and HCTZ was made using the ingredients set forth in Table 2 below.

TABLE 2

|   | Ingredient | (mg) | % |
|---|---|---|---|
| A | valsartan | 160.00 | 40.00 |
| B | hydrochlorothiazide | 12.50 | 3.13 |
| C | amlodipine besylate | 13.87* | 3.47 |
| D | microcrystalline cellulose | 147.63 | 36.91 |
| E | crospovidone | 54.00 | 13.50 |
| F | colloidal silicon dioxide | 3.00 | 0.75 |
| G | magnesium stearate (I) | 6.00 | 1.50 |
| H | magnesium stearate (II) | 3.00 | 0.75 |
|   | total | 400.00 |   |

*corresponds to 10 mg amlodipine free base

Ingredients A-G are placed into a diffusion blender and blended. Then, the blended material is sieved. Next, the sieved material is blended again in a diffusion blender. The blended/sieved material is then compacted using a roller compactor. The compacted material is milled through a screen and then blended with ingredient H in a diffusion blender. (This second blending step achieves the desired level of lubricant for the granulation and, in certain cases, combines sub-divided batches of ingredients A-G.) Next, the blended/milled material is compressed into monolayer solid dosage forms using a rotary tablet press, and the monolayer solid dosage forms are optionally film coated.

Ingredients A, C, D, E, F, and G are placed into a diffusion blender and blended. Then, the blended material is sieved. Next, the sieved material is blended again in a diffusion blender. The blended/sieved material is then compacted using a roller compactor. The compacted material is milled through a screen and then blended with ingredient B and H in a diffusion blender. (This second blending step achieves the desired level of B and H for the granulation and, in certain cases, combines sub-divided batches of ingredients A, C, D, E, F, and G.) Next, the blended/milled material is compressed into monolayer solid dosage forms using a rotary tablet press, and the monolayer solid dosage forms are optionally film coated.

Ingredients A, B, D, E, F, and G are placed into a diffusion blender and blended. Then, the blended material is sieved. Next, the sieved material is blended again in a diffusion blender. The blended/sieved material is then compacted using a roller compactor. The compacted material is milled through a screen and then blended with ingredient C and H in a diffusion blender. (This second blending step achieves the desired level of B and H for the granulation and, in certain cases, combines sub-divided batches of ingredients A, B, D, E, F, and G.) Next, the blended/milled material is compressed into monolayer solid dosage forms using a rotary tablet press, and the monolayer solid dosage forms are optionally film coated.

Ingredients A, D, E, F, and G are placed into a diffusion blender and blended. Then, the blended material is sieved. Next, the sieved material is blended again in a diffusion blender. The blended/sieved material is then compacted using a roller compactor. The compacted material is milled through a screen and then blended with ingredient B, C and H in a diffusion blender. (This second blending step achieves the desired level of B, C, and H for the granulation and, in certain cases, combines sub-divided batches of ingredients A, D, E, F, and G.) Next, the blended/milled material is compressed into monolayer solid dosage forms using a rotary tablet press, and the monolayer solid dosage forms are optionally film coated.

Example 3

160/25/10 Mg Tablet

A monolayer solid dosage form of valsartan, amlodipine and HCTZ was made using the ingredients set forth in Table 3 below.

TABLE 3

|   | Ingredient | (mg) | % |
|---|---|---|---|
| A | valsartan | 160.00 | 40.00 |
| B | hydrochlorothiazide | 25.00 | 6.25 |
| C | amlodipine besylate | 13.87* | 3.47 |
| D | microcrystalline cellulose | 135.13 | 33.78 |
| E | crospovidone | 54.00 | 13.50 |
| F | colloidal silicon dioxide | 3.00 | 0.75 |
| G | magnesium stearate (I) | 6.00 | 1.50 |
| H | magnesium stearate (II) | 3.00 | 0.75 |
|   | total | 400.00 |   |

*corresponds to 10 mg amlodipine free base

Ingredients A-G are placed into a diffusion blender and blended. Then, the blended material is sieved. Next, the sieved material is blended again in a diffusion blender. The blended/sieved material is then compacted using a roller compactor. The compacted material is milled through a screen and then blended with ingredient H in a diffusion blender. (This second blending step achieves the desired level of lubricant for the granulation and, in certain cases, combines sub-divided batches of ingredients A-G.) Next, the blended/milled material is compressed into monolayer solid dosage forms using a rotary tablet press, and the monolayer solid dosage forms are optionally film coated.

Ingredients A, C, D, E, F, and G are placed into a diffusion blender and blended. Then, the blended material is sieved. Next, the sieved material is blended again in a diffusion blender. The blended/sieved material is then compacted using a roller compactor. The compacted material is milled through a screen and then blended with ingredient B and H in a diffusion blender. (This second blending step achieves the desired level of B and H for the granulation and, in certain cases, combines sub-divided batches of ingredients A, C, D, E, F, and G.) Next, the blended/milled material is compressed into monolayer solid dosage forms using a rotary tablet press, and the monolayer solid dosage forms are optionally film coated.

Ingredients A, B, D, E, F, and G are placed into a diffusion blender and blended. Then, the blended material is sieved. Next, the sieved material is blended again in a diffusion blender. The blended/sieved material is then compacted using a roller compactor. The compacted material is milled through a screen and then blended with ingredient C and H in a diffusion blender. (This second blending step achieves the desired level of B and H for the granulation and, in certain cases, combines sub-divided batches of ingredients A, B, D, E, F, and G.) Next, the blended/milled material is compressed into monolayer solid dosage forms using a rotary tablet press, and the monolayer solid dosage forms are optionally film coated.

Ingredients A, D, E, F, and G are placed into a diffusion blender and blended. Then, the blended material is sieved. Next, the sieved material is blended again in a diffusion blender. The blended/sieved material is then compacted using a roller compactor. The compacted material is milled through a screen and then blended with ingredient B, C and H in a diffusion blender. (This second blending step achieves the desired level of B, C, and H for the granulation and, in certain cases, combines sub-divided batches of ingredients A, D, E, F, and G.) Next, the blended/milled material is compressed into monolayer solid dosage forms using a rotary tablet press, and the monolayer solid dosage forms are optionally film coated.

Example 4

160/25/5 Mg Tablet

A monolayer solid dosage form of valsartan, amlodipine and HCTZ was made using the ingredients set forth in Table 4 below.

TABLE 4

|   | Ingredient | (mg) | % |
|---|---|---|---|
| A | valsartan | 160.00 | 40.00 |
| B | hydrochlorothiazide | 25.00 | 6.25 |
| C | amlodipine besylate | 6.94* | 1.74 |
| D | microcrystalline cellulose | 142.06 | 35.51 |
| E | crospovidone | 54.00 | 13.50 |
| F | colloidal silicon dioxide | 3.00 | 0.75 |
| G | magnesium stearate (I) | 6.00 | 1.50 |
| H | magnesium stearate (II) | 3.00 | 0.75 |
|   | total | 400.00 |   |

*corresponds to 5 mg amlodipine free base

Ingredients A-G are placed into a diffusion blender and blended. Then, the blended material is sieved. Next, the sieved material is blended again in a diffusion blender. The blended/sieved material is then compacted using a roller compactor. The compacted material is milled through a screen and then blended with ingredient H in a diffusion blender. (This second blending step achieves the desired level of lubricant for the granulation and, in certain cases, combines sub-divided batches of ingredients A-G.) Next, the blended/milled material is compressed into monolayer solid dosage forms using a rotary tablet press, and the monolayer solid dosage forms are optionally film coated.

Ingredients A, C, D, E, F, and G are placed into a diffusion blender and blended. Then, the blended material is sieved. Next, the sieved material is blended again in a diffusion blender. The blended/sieved material is then compacted using a roller compactor. The compacted material is milled through a screen and then blended with ingredient B and H in a diffusion blender. (This second blending step achieves the desired level of B and H for the granulation and, in certain cases, combines sub-divided batches of ingredients A, C, D, E, F, and G.) Next, the blended/milled material is compressed into monolayer solid dosage forms using a rotary tablet press, and the monolayer solid dosage forms are optionally film coated.

Ingredients A, B, D, E, F, and G are placed into a diffusion blender and blended. Then, the blended material is sieved. Next, the sieved material is blended again in a diffusion blender. The blended/sieved material is then compacted using a roller compactor. The compacted material is milled through a screen and then blended with ingredient C and H in a diffusion blender. (This second blending step achieves the desired level of B and H for the granulation and, in certain cases, combines sub-divided batches of ingredients A, B, D, E, F, and G.) Next, the blended/milled material is compressed into monolayer solid dosage forms using a rotary tablet press, and the monolayer solid dosage forms are optionally film coated.

Ingredients A, D, E, F, and G are placed into a diffusion blender and blended. Then, the blended material is sieved. Next, the sieved material is blended again in a diffusion blender. The blended/sieved material is then compacted using a roller compactor. The compacted material is milled through a screen and then blended with ingredient B, C and H in a diffusion blender. (This second blending step achieves the desired level of B, C, and H for the granulation and, in certain cases, combines sub-divided batches of ingredients A, D, E, F, and G.) Next, the blended/milled material is compressed into monolayer solid dosage forms using a rotary tablet press, and the monolayer solid dosage forms are optionally film coated.

Ingredients A-G are placed into a diffusion blender and blended. Then, the blended material is sieved. Next, the sieved material is blended again in a diffusion blender. The blended/sieved material is then compacted using a roller compactor. The compacted material is milled through a screen and then blended with ingredient H in a diffusion blender. (This second blending step achieves the desired level of lubricant for the granulation and, in certain cases, combines sub-divided batches of ingredients A-G.) Next, the blended/milled material is compressed into monolayer solid dosage forms using a rotary tablet press, and the monolayer solid dosage forms are optionally film coated.

Ingredients A, C, D, E, F, and G are placed into a diffusion blender and blended. Then, the blended material is sieved. Next, the sieved material is blended again in a diffusion blender. The blended/sieved material is then compacted using a roller compactor. The compacted material is milled through a screen and then blended with ingredient B and H in a diffusion blender. (This second blending step achieves the desired level of B and H for the granulation and, in certain cases, combines sub-divided batches of ingredients A, C, D, E, F, and G.) Next, the blended/milled material is compressed into monolayer solid dosage forms using a rotary tablet press, and the monolayer solid dosage forms are optionally film coated.

Ingredients A, B, D, E, F, and G are placed into a diffusion blender and blended. Then, the blended material is sieved. Next, the sieved material is blended again in a diffusion blender. The blended/sieved material is then compacted using a roller compactor. The compacted material is milled through a screen and then blended with ingredient C and H in a diffusion blender. (This second blending step achieves the desired level of B and H for the granulation and, in certain cases, combines sub-divided batches of ingredients A, B, D, E, F, and G.) Next, the blended/milled material is compressed into monolayer solid dosage forms using a rotary tablet press, and the monolayer solid dosage forms are optionally film coated.

Ingredients A, D, E, F, and G are placed into a diffusion blender and blended. Then, the blended material is sieved. Next, the sieved material is blended again in a diffusion blender. The blended/sieved material is then compacted using a roller compactor. The compacted material is milled through a screen and then blended with ingredient B, C and H in a diffusion blender. (This second blending step achieves the desired level of B, C, and H for the granulation and, in certain cases, combines sub-divided batches of ingredients A, D, E, F, and G.) Next, the blended/milled material is compressed into monolayer solid dosage forms using a rotary tablet press, and the monolayer solid dosage forms are optionally film coated.

Example 5

320/25/10 Mg Tablet

A monolayer solid dosage form of valsartan, amlodipine and HCTZ was made using the ingredients set forth in Table 5 below.

TABLE 5

|   | Ingredient | (mg) | % |
|---|---|---|---|
| A | valsartan | 320.00 | 40.00 |
| B | hydrochlorothiazide | 25.00 | 3.13 |
| C | amlodipine besylate | 13.87* | 1.73 |
| D | microcrystalline cellulose | 309.12 | 38.64 |
| E | crospovidone | 108.00 | 13.50 |
| F | colloidal silicon dioxide | 6.00 | 0.75 |
| G | magnesium stearate (I) | 12.00 | 1.50 |
| H | magnesium stearate (II) | 6.00 | 0.75 |
|   | total | 800.00 |   |

*corresponds to 10 mg amlodipine free base

Example 6

160/12.5/5; 160/12.5/10; 160/25/5; 160/25/10 and 320/25/10 Mg Tablet

A bilayer solid dosage form of valsartan, amlodipine and HCTZ was made using the ingredients set forth in Table 6 below.

TABLE 6

|   | Ingredient | (mg) | % |
|---|---|---|---|
| valsartan/hydrochlorothiazide layer | | | |
| A | valsartan | 320.00 | 35.56 |
| B | hydrochlorothiazide | 25.00 | 2.78 |

TABLE 6-continued

| | Ingredient | (mg) | % |
|---|---|---|---|
| C | microcrystalline cellulose | 151.00 | 16.78 |
| D | crospovidone | 80.00 | 8.89 |
| E | colloidal silicon dioxide | 6.00 | 0.67 |
| F | magnesium stearate (I) | 12.00 | 1.33 |
| G | magnesium stearate (II) | 6.00 | 0.67 |
| | subtotal | 600.00 | |
| | amlodipine layer | | |
| H | amlodipine besylate | 13.87* | 1.54 |
| I | microcrystalline cellulose | 279.03 | 31.00 |
| J | sodium starch glycolate | 6.00 | 0.67 |
| K | colorant | 0.20 | 0.02 |
| L | magnesium stearate (III) | 0.30 | 0.03 |
| M | magnesium stearate (IV) | 0.60 | 0.07 |
| | subtotal | 300.00 | |
| | total | 900.00 | |

*corresponds to 10 mg amlodipine free base

First, the valsartan is granulated by combining ingredients A-F in a diffusion blender. Then, the blended material is sieved through a screen. Next, the sieved material is blended again in a diffusion blender. The blended/sieved material is then compacted using a roller compactor. The compacted material is milled through a screen and then blended with ingredient G in a diffusion blender. (This second blending step achieves the desired level of lubricant for the granulation and, in certain cases, combines sub-divided batches of ingredients A-F.)

Second, the amlodipine besylate is granulated by combining ingredients H-L in a diffusion blender. Then, the blended material is sieved through a screen. Next, the sieved material is blended again in a diffusion blender. The blended/sieved material is then compacted using a roller compactor. The compacted material is milled through a screen and then blended with ingredient M in a diffusion blender. (This second blending step achieves the desired level of lubricant for the granulation and, in certain cases, combines sub-divided batches of ingredients H-L.)

Finally, the valsartan granulation and the amlodipine granulation are compressed into bilayer solid dosage forms using a bilayer rotary tablet press, and the bilayer solid dosage forms are optionally film coated.

Example 7

160/12.5/5; 160/12.5/10; 160/25/5; 160/25/10 and 160/12.5/5 Mg Tablet

A bilayer solid dosage form of valsartan, amlodipine and HCTZ was made using the ingredients set forth in Table 8 and 9 below.

TABLE 7

| | | 160/25/10 mg | | 160/25/5 mg | | 160/12.5/5 mg | | 160/12.5/10 mg | |
|---|---|---|---|---|---|---|---|---|---|
| | Ingredient | mg/unit | % | mg/unit | % | mg/unit | % | mg/unit | % |
| | Valsartan and HCTZ layer | | | | | | | | |
| A | Valsartan DS | 160.00 | 26.67 | 160.00 | 35.56 | 160.00 | 35.56 | 160.00 | 26.67 |
| B | HCTZ | 25.00 | 4.17 | 25.00 | 5.56 | 12.50 | 2.78 | 12.50 | 2.08 |
| C | Avicel 102 | 63.00 | 10.50 | 63.00 | 14.00 | 85.50 | 19.00 | 85.50 | 14.25 |
| D | Crospovidone | 40.00 | 6.67 | 40.00 | 8.89 | 30.00 | 6.67 | 30.00 | 5.00 |
| E | Cab-O-Sil | 3.00 | 0.50 | 3.00 | 0.67 | 3.00 | 0.67 | 3.00 | 0.50 |
| F | Mag. St.(I) | 6.00 | 1.00 | 6.00 | 1.33 | 6.00 | 1.33 | 6.00 | 1.00 |
| G | Mag. St.(II) | 3.00 | 0.50 | 3.00 | 0.67 | 3.00 | 0.67 | 3.00 | 0.50 |
| | Sub-total | 300.00 | | 300.00 | | 300.00 | | 300.00 | |
| | Amlodipine layer | | | | | | | | |
| H | Amlodipine Besylate | 13.87[a] | 2.31 | 6.94[b] | 1.54 | 6.94[b] | 1.54 | 13.87[a] | 2.31 |
| I | Avicel PH102 | 279.03 | 46.51 | 139.51 | 31.00 | 139.51 | 31.00 | 279.03 | 46.51 |
| J | Sodium Starch Glycolate | 6.00 | 1.00 | 3.00 | 0.67 | 3.00 | 0.67 | 6.00 | 1.00 |
| K | Iron oxide yellow | 0.20 | 0.03 | 0.10 | 0.02 | 0.10 | 0.02 | 0.20 | 0.03 |
| L | Mag. St. (III) | 0.30 | 0.05 | 0.15 | 0.03 | 0.15 | 0.03 | 0.30 | 0.05 |
| M | Mag. St. (IV) | 0.60 | 0.10 | 0.30 | 0.07 | 0.30 | 0.07 | 0.60 | 0.10 |
| | Sub-total | 300.00 | | 150.00 | | 150.00 | | 300.00 | |
| | Total | 600.00 | 100.00 | 450.00 | 100.00 | 450.00 | 100.00 | 600.00 | 100.00 |

[a]corresponds to 10 mg amlodipine free base;
[b]corresponds to 5 mg amlodipine free base

TABLE 8

| | Ingredient | (mg) | % |
|---|---|---|---|
| | valsartan layer | | |
| A | valsartan | 160.00 | 34.78 |
| B | microcrystalline cellulose | 108.00 | 23.48 |
| C | crospovidone | 30.00 | 6.52 |
| D | colloidal silicon dioxide | 3.00 | 0.65 |
| E | magnesium stearate (I) | 6.00 | 1.30 |
| F | magnesium stearate (II) | 3.00 | 0.65 |
| | subtotal | 310.00 | |

TABLE 8-continued

| | Ingredient | (mg) | % |
|---|---|---|---|
| | amlodipine/hydrochlorothiazide layer | | |
| G | amlodipine besylate | 6.94* | 1.51 |
| H | hydrochlorothiazide | 12.50 | 2.72 |
| I | microcrystalline cellulose | 127.02 | 27.61 |
| J | sodium starch glycolate | 3.00 | 0.65 |
| K | colorant | 0.10 | 0.02 |
| L | magnesium stearate (III) | 0.15 | 0.03 |
| M | magnesium stearate (IV) | 0.30 | 0.07 |
| | subtotal | 150.00 | |
| | total | 460.00 | |

*corresponds to 5 mg amlodipine free base

TABLE 9

| | | 160/25/10 mg | | 160/25/5 mg | | 160/12.5/10 mg | | 320/25/10 mg | |
|---|---|---|---|---|---|---|---|---|---|
| | Ingredient | mg/unit | % | mg/unit | % | mg/unit | % | mg/unit | % |
| | Valsartan layer | | | | | | | | |
| A | Valsartan DS | 160.00 | 26.23 | 160.00 | 26.23 | 160.00 | 26.23 | 320.00 | 34.78 |
| B | Avicel 102 | 108.00 | 17.70 | 108.00 | 17.70 | 108.00 | 17.70 | 216.00 | 23.48 |
| C | Crospovidone | 30.00 | 4.92 | 30.00 | 4.92 | 30.00 | 4.92 | 60.00 | 6.52 |
| D | Cab-O-Sil | 3.00 | 0.49 | 3.00 | 0.49 | 3.00 | 0.49 | 6.00 | 0.65 |
| E | Mag. St.(I) | 6.00 | 0.98 | 6.00 | 0.98 | 6.00 | 0.98 | 12.00 | 1.30 |
| F | Mag. St.(II) | 3.00 | 0.49 | 3.00 | 0.49 | 3.00 | 0.49 | 6.00 | 0.65 |
| | Sub-total | 310.00 | | 310.00 | | 310.00 | | 620.00 | |
| | Amlodipine and HCTZ layer | | | | | | | | |
| G | Amlodipine Besylate | 13.87 | 2.27 | 6.94 | 1.14 | 13.87 | 2.27 | 13.87 | 1.51 |
| H | HCTZ | 25.00 | 4.10 | 25.00 | 4.10 | 12.50 | 2.05 | 25.00 | 2.72 |
| I | Avicel PH102 | 254.03 | 41.64 | 260.96 | 42.78 | 266.53 | 43.69 | 254.03 | 27.61 |
| J | Sodium Starch Glycolate | 6.00 | 0.98 | 6.00 | 0.98 | 6.00 | 0.98 | 6.00 | 0.65 |
| K | Iron oxide yellow | 0.20 | 0.03 | 0.20 | 0.03 | 0.20 | 0.03 | 0.20 | 0.02 |
| L | Mag. St. (III) | 0.30 | 0.05 | 0.30 | 0.05 | 0.30 | 0.05 | 0.30 | 0.03 |
| M | Mag. St. (IV) | 0.60 | 0.10 | 0.60 | 0.10 | 0.60 | 0.10 | 0.60 | 0.07 |
| | Sub-total | 300.00 | | 300.00 | | 300.00 | | 300.00 | |
| | Total | 610.00 | 100.00 | 610.00 | 100.00 | 610.00 | 100.00 | 920.00 | 100.00 |

First, the valsartan is granulated by combining ingredients A-E in a diffusion blender. Then, the blended material is sieved through a screen. Next, the sieved material is blended again in a diffusion blender. The blended/sieved material is then compacted using a roller compactor. The compacted material is milled through a screen and then blended with ingredient F in a diffusion blender. (This second blending step achieves the desired level of lubricant for the granulation and, in certain cases, combines sub-divided batches of ingredients A-E.)

Second, the amlodipine besylate is granulated by combining ingredients G-L in a diffusion blender. Then, the blended material is sieved through a screen. Next, the sieved material is blended again in a diffusion blender. The blended/sieved material is then compacted using a roller compactor. The compacted material is milled through a screen and then blended with ingredient M in a diffusion blender. (This second blending step achieves the desired level of lubricant for the granulation and, in certain cases, combines sub-divided batches of ingredients G-L.)

Finally, the valsartan granulation and the amlodipine granulation are compressed into bilayer solid dosage forms using a bilayer rotary tablet press, and the bilayer solid dosage forms are optionally film coated.

Example 8

160/12.5/5; 160/12.5/10; 160/25/5; 160/25/10 and 320/25/10 Mg Tablet

A bilayer solid dosage form of valsartan, amlodipine and HCTZ was made using the ingredients set forth in Table 10 and 11 below.

TABLE 10

| | | 160/25/10 mg | | 160/25/5 mg | |
|---|---|---|---|---|---|
| | Ingredient | mg/unit | % | mg/unit | % |
| | Valsartan and amlodipine layer | | | | |
| A | Valsartan DS | 160.00 | 25.24 | 160.00 | 25.48 |
| B | Amlodipine besylate | 13.87 | 2.19 | 6.94 | 1.10 |
| C | Avicel PH102 | 108.13 | 17.06 | 109.07 | 17.37 |
| D | Crospovidone XL | 40.00 | 6.31 | 40.00 | 6.37 |
| E | Cab-o-sil | 3.00 | 0.47 | 3.00 | 0.48 |
| F | Mg. Stearate (I) | 6.00 | 0.95 | 6.00 | 0.96 |
| G | Mg. Stearate (I) | 3.00 | 0.47 | 3.00 | 0.48 |
| | Sub-total | 334.00 | | 328.00 | |
| | HCTZ layer | | | | |
| H | HCTZ | 25.00 | 3.94 | 25.00 | 3.98 |
| I | Avicel PH102 | 267.90 | 42.26 | 267.90 | 42.66 |
| J | Sodium Starch Glycolate | 6.00 | 0.95 | 6.00 | 0.96 |

TABLE 10-continued

| | | 160/25/10 mg | | 160/25/5 mg | |
|---|---|---|---|---|---|
| | Ingredient | mg/unit | % | mg/unit | % |
| K | Iron oxide yellow | 0.20 | 0.03 | 0.20 | 0.03 |
| L | Mag. St. (Ill) | 0.30 | 0.05 | 0.30 | 0.05 |
| M | Mag. St. (IV) | 0.60 | 0.09 | 0.60 | 0.10 |
| | Sub-total | 300.00 | | 300.00 | |
| | Total | 634.00 | 100.00 | 628.00 | 100.00 |

TABLE 11

| | | 160/12.5/5 mg | | 160/12.5/10 mg | | 320/25/10 mg | |
|---|---|---|---|---|---|---|---|
| | Ingredient | mg/unit | % | mg/unit | % | mg/unit | % |
| | Valsartan and amlodipine layer | | | | | | |
| A | Valsartan DS | 160.00 | 33.06 | 160.00 | 25.48 | 320.00 | 33.47 |
| B | Amlodipine besylate | 13.87 | 2.87 | 6.94 | 1.10 | 13.87 | 1.45 |
| C | Avicel PH102 | 108.13 | 22.34 | 109.07 | 17.37 | 218.13 | 22.82 |
| D | Crospovidone XL | 40.00 | 8.26 | 40.00 | 6.37 | 80.00 | 8.37 |
| E | Cab-o-sil | 3.00 | 0.62 | 3.00 | 0.48 | 6.00 | 0.63 |
| F | Mg. Stearate (I) | 6.00 | 1.24 | 6.00 | 0.96 | 12.00 | 1.26 |
| G | Mg. Stearate (I) | 3.00 | 0.62 | 3.00 | 0.48 | 6.00 | 0.63 |
| | Sub-total | 334.00 | | 328.00 | | 656.00 | |
| | HCTZ layer | | | | | | |
| H | HCTZ | 12.50 | 2.58 | 12.50 | 1.99 | 25.00 | 2.62 |
| I | Avicel PH102 | 133.95 | 27.68 | 280.40 | 44.65 | 267.90 | 28.02 |
| J | Sodium Starch Glycolate | 3.00 | 0.62 | 6.00 | 0.96 | 6.00 | 0.63 |
| K | Iron oxide yellow | 0.10 | 0.02 | 0.20 | 0.03 | 0.20 | 0.02 |
| L | Mag. St. (III) | 0.15 | 0.03 | 0.30 | 0.05 | 0.30 | 0.03 |
| M | Mag. St. (IV) | 0.30 | 0.06 | 0.60 | 0.10 | 0.60 | 0.06 |
| | Sub-total | 150.00 | | 300.00 | | 300.00 | |
| | Total | 484.00 | 100.00 | 628.00 | 100.00 | 956.00 | 100.00 |

First, the valsartan is granulated by combining ingredients A-F in a diffusion blender. Then, the blended material is sieved through a screen. Next, the sieved material is blended again in a diffusion blender. The blended/sieved material is then compacted using a roller compactor. The compacted material is milled through a screen and then blended with ingredient G in a diffusion blender. (This second blending step achieves the desired level of lubricant for the granulation and, in certain cases, combines sub-divided batches of ingredients A-F.)

Second, the HCTZ is granulated by combining ingredients H-L in a diffusion blender. Then, the blended material is sieved through a screen. Next, the sieved material is blended again in a diffusion blender. The blended/sieved material is then compacted using a roller compactor. The compacted material is milled through a screen and then blended with ingredient M in a diffusion blender. (This second blending step achieves the desired level of lubricant for the granulation and, in certain cases, combines sub-divided batches of ingredients H-L.)

Finally, the valsartan granulation and the amlodipine granulation are compressed into bilayer solid dosage forms using a bilayer rotary tablet press, and the bilayer solid dosage forms are optionally film coated.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entirety.

What is claimed is:

1. A solid dosage form comprising:
   valsartan;
   amlodipine;
   hydrochlorothiazide; and
   pharmaceutically acceptable additives suitable for the preparation of solid dosage forms of valsartan, wherein the solid dosage form of valsartan/hydrochlorothiazide/amlodipine is selected from 160 mg/12.5 mg/5 mg, 160 mg/12.5 mg/10 mg, 160 mg/25 mg/10 mg, 160 mg/25 mg/5 mg and 320 mg/25 mg/10 mg, said solid dosage either in the form of a monolayer tablet or a bilayer tablet.

2. The solid dosage form of claim 1, wherein the amlodipine is provided in the form of amlodipine besylate.

3. The solid dosage form of claim 1, wherein the solid dosage form takes the form of a monolayer tablet.

4. The solid dosage form of claim 1, wherein the solid dosage form takes the form of a bilayer tablet.

5. The solid dosage form of claim 4, wherein the bilayer tablet has the valsartan and the hydrochlorothiazide in a first layer and the amlodipine in a second layer.

6. The solid dosage form of claim 4, wherein the bilayer tablet has the valsartan in a first layer and the amlodipine and the hydrochlorothiazide in a second layer.

7. The solid dosage form of claim 1, wherein the pharmaceutically acceptable additives are selected from the group consisting of diluents, disintegrants, glidants, lubricants, binders, colorants and combinations thereof.

\* \* \* \* \*